United States Patent
Nazerian

(10) Patent No.: US 6,235,049 B1
(45) Date of Patent: May 22, 2001

(54) DEVICE FOR HEAT TREATMENT

(76) Inventor: Farzam Nazerian, Diagnosvagen 15 C, 2 tr, Huddinge (SE)

( * ) Notice: Subject to any disclaimer, the term of this patent is extended or adjusted under 35 U.S.C. 154(b) by 0 days.

(21) Appl. No.: 09/230,134

(22) PCT Filed: Jul. 15, 1997

(86) PCT No.: PCT/SE97/01287

§ 371 Date: Jan. 19, 1999

§ 102(e) Date: Jan. 19, 1999

(87) PCT Pub. No.: WO98/03135

PCT Pub. Date: Jan. 29, 1998

(30) Foreign Application Priority Data

Jul. 19, 1996 (SE) .................................................. 9602819

(51) Int. Cl.[7] .................................................. A61F 7/00
(52) U.S. Cl. .......................... 607/108; 607/112; 607/99; 607/98
(58) Field of Search ................... 607/98, 99, 108, 607/96, 112

(56) References Cited

U.S. PATENT DOCUMENTS

| | | | |
|---|---|---|---|
| 3,839,621 | * 10/1974 | Hariu | 219/211 |
| 4,279,255 | * 7/1981 | Hoffman | 128/402 |
| 4,628,930 | * 12/1986 | Williams | 128/379 |
| 4,753,241 | * 6/1988 | Brannigan et al. | 128/380 |
| 5,050,595 | * 9/1991 | Krafft | 128/379 |
| 5,062,414 | * 11/1991 | Grim | 128/68.1 |
| 5,336,255 | * 8/1994 | Kanare et al. | 607/149 |
| 5,378,225 | * 1/1995 | Chatman, Jr. et al. | 602/19 |
| 5,800,490 | * 9/1998 | Patz et al. | 607/108 |
| 5,837,005 | * 11/1998 | Viltro et al. | 607/112 |
| 6,048,326 | * 4/2000 | Davis et al. | 602/26 |

OTHER PUBLICATIONS http://www.birch.net/~swtech/Therapy.htm.*

* cited by examiner

Primary Examiner—John P. Leubecker
Assistant Examiner—Jocelyn Debra Ram
(74) Attorney, Agent, or Firm—Michaelson & Wallace; Peter L. Michaelson

(57) ABSTRACT

A device for a heat treatment of a body part, comprising a heating element (1) and means (2) for holding the heating element against the body part to be heat-treated. The heat element (1) comprises a plurality of separate heating cells (6) and is flexible in such a manner that it may be adapted to abut said body part.

9 Claims, 3 Drawing Sheets

DEVICE FOR HEAT TREATMENT

TECHNICAL FIELD OF THE INVENTION AND PRIOR ART

The present invention relates to a device for heat treatment of a body part, comprising a heating element and means for holding the heating element against the body part to be heat-treated.

It is known to use heat for the treatment of infections, muscular ache and different deceases, such as fibromyalgia and rheumatism. Thereby, heat baths and different types of heating pads and the like are used. Such known heat pads often have the disadvantage that they are ungainly and not suitable to be carried against the body, if the patient wants to move. The freedom of movement of the patients is therefore very restricted and this makes the possibilities of the treatment of patients during a longer time period more difficult. A common type of heating pad is intended to be placed in a bed and presupposes that the patient is lying down during the treatment.

U.S. Pat. No. 3,108,596 shows a heating pad comprising an embodied electric heating coil. This is intended to be energized by means of a battery with a relatively low voltage so that it may be attached close to the skin without risk of electrical shocks. The heating pad is intended to be attached against the body by means of elastic bands or the like.

U.S. Pat. No. 2,467,447 shows a liquid container in the shape of a bottle having a concave shape and which may be attached to cover, for example, a portion of the upper arm. Furthermore, the bottle comprises strings by which it may be fastened to said portion of the upper arm. Furthermore, the bottle comprises an electric heating element for heating of the liquid enclosed in the bottle. The bottle is manufactured in a material being flexible per se, such as rubber, but it has a relatively stiff shape, and therefore it may not be suited in a flexible way to different body parts or to different individuals.

U.S. Pat. No. 5,073,688 shows a blanket with an embodied heating coil. This consists of either an electric wire or a tubular conduit for transportation of a heated liquid.

U.S. Pat. No. 4,628,930 shows a heating pad comprising an electric heating coil for heating of the lower abdomen. The heating pad consists of a part of a pair of briefs which, consequently, function as an attachment member for holding the heating pad against the lower abdomen. The power for the heating coil is intended to be supplied by means of a battery provided in the briefs.

SUMMARY OF THE INVENTION

The object of the present invention is to remedy the above-mentioned problems and provide a device for heat treatment which may be carried by a patient without restricting the freedom of movement of the patient.

This object is achieved by the device initially defined and characterized in that the heating element comprises a plurality of separate heating cells and is flexible in such a manner that it may be adapted to abut said body part. By being constructed of a plurality of separate cells, the heating element is more flexible and bendable, and may, consequently, in a simple way be bent and shaped to abut a great portion of the surface of the body part to be heat-treated.

According to one embodiment of the invention, essentially each heating cell comprises a heating member and means for heat storage. Thereby, a more uniform distribution of the heat may be provided. Even if the supply of electric current occasionally is missing, the treatment does not need to be interrupted. Thereby, the heating member may comprise an electric heating coil. By such a device, an effective heating may be provided either by the network or by means of electric batteries. Furthermore, the heat storage means may comprise a liquid, for example at least any one of water, a mixture comprising glycerol, a mixture comprising oil or any oil-like substance, and a salt solution. Such a liquid also contributes to the possibility of the relatively concentrated heat from the electric coil being distributed to a greater area. Advantageously, essentially each heating cell forms an essentially closed inner space, in which the heat storage means is enclosed.

According to another embodiment of the invention, essentially each heating cell comprises a wall, which defines the inner space and which is manufactured of a flexible material. Thereby, the heating cells do not need to be absolutely stiff but they may be adapted to the body part they are to abut.

According to another embodiment of the invention, the heating cells are connected to each other by a flexible connection. According to another embodiment, the heating element comprises an extensible, flexible support member, to which the heating cells are provided. Thereby, the support member may advantageously comprise said flexible connection. Furthermore, the heating cells may be provided on the support member side by side with an interspace between adjacent heating cells. In such a way, a high flexibility of the heating element is obtained.

According to a further embodiment of the invention, said holding means comprises an extensible, flexible material, for example fabric, at which the support member is arranged to be attached by a hook-and-loop attachment member, for example a VELCRO connection. Advantageously, the flexible material of the holding means may have a shape adapted to the body part, to which the heating element is to be applied. Consequently, one and the same heating element may be used together with different attachment means for the treatment of different body parts.

According to another embodiment of the invention, said holding means comprises at least one locking element intended to extend around said body part. Thereby, the locking member may be arranged to be locked releasably, using a hook-and-loop fastener for example by means of a VELCRO-connection.

BRIEF DESCRIPTION OF THE DRAWINGS

The present invention is now to be explained by means of different embodiments shown by way of example, and with reference to the attached drawings.

DETAILED DESCRIPTION OF DIFFERENT EMBODIMENTS

Figure 1:
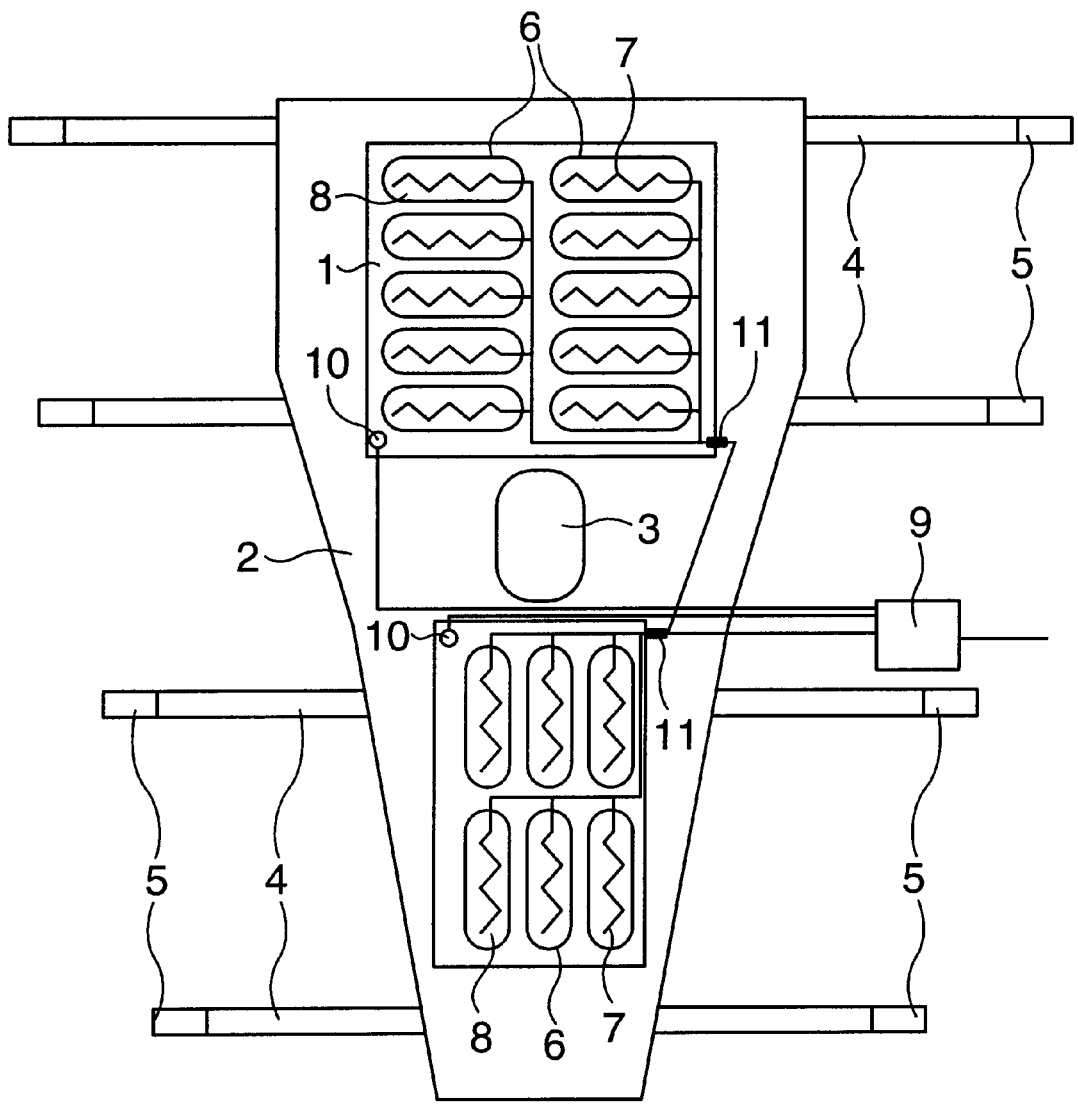
FIG. 1 shows a front view of an embodiment of the device according to the invention.

FIG. 1 shows a device for heat treatment according to the invention, which comprises two heating elements 1 and means 2 for holding these against the body part of a patient, which is to be treated. These holding means 2 comprise an extensible, bendable, flexible piece in a suitable material, for example plastic or fabric which may be carried against the body in a comfortable way. This piece 2 has a shape adapted to the body part on which the heating element 1 is to be applied. In the shown example, the piece 2 is provided to be attached to an arm. Thereby, the piece 2 has a centrally provided hole 3 through which the elbow of the patient may extend when the patient bends the arm. Furthermore, the piece 2 comprises four locking members 4 which are intended to extend around the arm to be treated for attaching the device thereto. Each locking member 4 comprises two bands with hoop-and-loop fasteners 5, e.g. a so called VELCRO-connection and is arranged to be locked releasably by means thereof. Also other types of locking members may of course be used, for example different types of buttons or hooks.

Each heating element 1 comprises a plurality of separate, individual heating cells 6, each comprising a heating member 7 in the shape of an electric heating coil with an electric resistance wire. Furthermore, each heating cell 6 comprises an essentially closed inner space 8 in which the heating member 7 is located and in which a means for heat storage is enclosed. Each heating member 7 is, by means of a connection in parallel, connected to a schematically shown control unit 9 which in turn may be connected directly to the network or to a battery (not shown). Furthermore, the heating element 1 comprises a temperature sensor 10 also connected to the control unit 9. By means of the control unit 9, a suitable temperature may be adjusted and by means of the temperature sensor 10, the temperature level may be kept essentially constant. Furthermore, each heating element 1 comprises a schematically shown overload protection 11 which breaks the current at too high a load for reasons of security.

Figure 2:
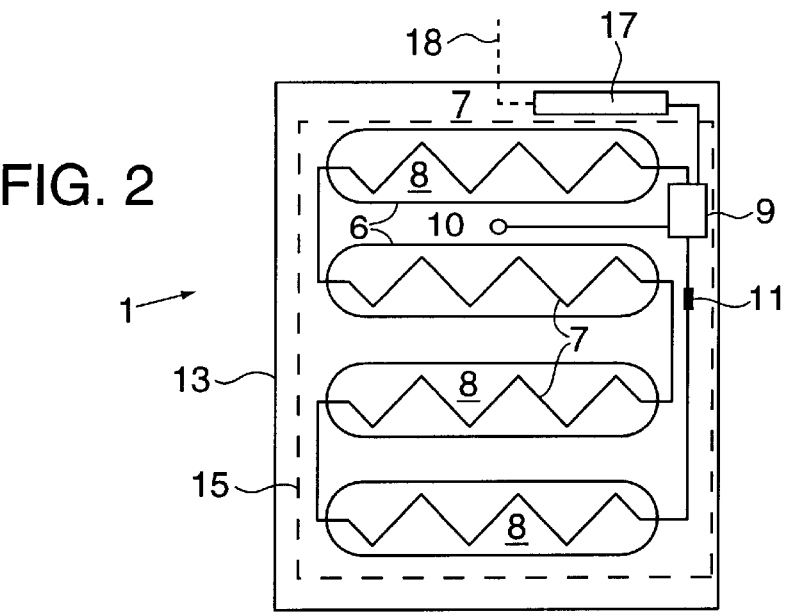
FIG. 2 shows a front view of a heating element of an embodiment of the device according to the invention.
Figure 3:
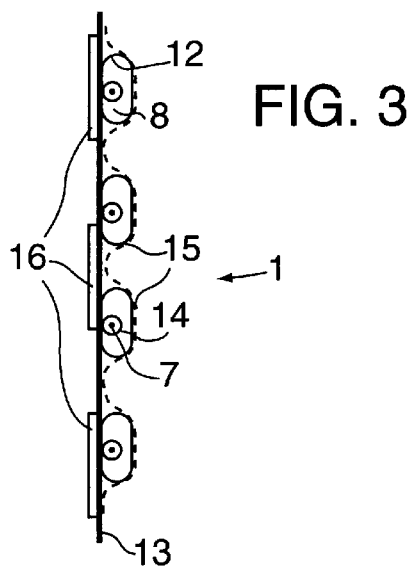
FIG. 3 shows a side view of the heating element in FIG. 2.
Figure 4:
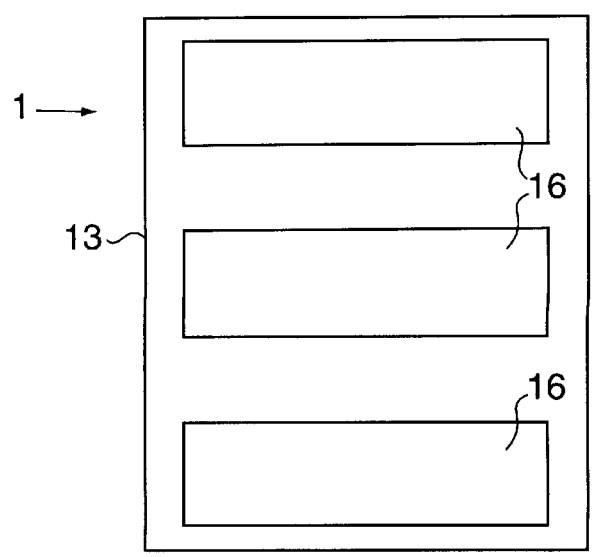
FIG. 4 shows a rear view of the heating element in FIG. 2.

The heating element 1 is now to be described more in detail with reference to FIGS. 2–4, which show a further embodiment of the invention. It shall be noted that for components with a corresponding function, the same reference signs have been used in all embodiments shown. In contrast to the embodiment shown in FIG. 1, the electric heating coils 7 of the heating element 1 according to the embodiment in FIGS. 2–4 are connected in series. The heating element 1 shown in FIGS. 2–4 comprises four heating cells 6. It shall be noted that the heating element 1 according to the invention may be provided with an arbitrary number of such heating cells 6.

As further appears from FIGS. 2–4, each separate heating cell 6 comprises a wall 12 defining the inner space 8. This wall 12 is manufactured in a flexible, bendable material. This wall 12 is to be as thin as possible for obtaining a good heat transfer and this material is to have a good heat transfer ability. The means for heat storage, which is enclosed in the space 8, comprises a liquid, for example at least any one of water, a mixture comprising glycerol, a mixture comprising oil or any oil-like substance, and a salt solution. This liquid is, except the ability of each storage, also able to transfer heat from the heating member 7 and distribute it uniformly to the body part to be treated. Furthermore, the heating element 1 comprises an extensible, bendable, flexible support member 13 which is thin in relation to its extension. On one side of this support member 13, the heating cells 6 are provided side by side with an interspace between each heating cell 6. In such a way, the support member may quite simply be bent at least in the areas between the heating cells 6. It shall be noted that the heating cells 6 may have another shape than the elongated one shown. They may for instance be circular, oval or square.

The cross-section shape of the heating cells 6 appears from FIG. 3. Therein, an electric insulating layer 14 is also indicated schematically, which encloses the electric resistance wire 7 and which insulates electrically the latter against the liquid present in the inner space 8.

Furthermore, a bendable, flexible cover layer 15 is provided over the heating cells for protection of the heating cells 6 and for keeping them safely in place on the support member 13. This cover layer 15 is very thin in relation to its extension and is manufactured in a suitable material, for example plastic which makes a good heat transfer possible. The support member 13 is suitably manufactured of a material with good heat-insulating ability for preventing loss of heat. Three attachment members 16 are provided on the other side of the support member 13 for making the attachment of the heat element 1 to the holding means 2 possible. This attachment member 16 may be a hook-and-loop fastener such as a VELCRO-connection.

The embodiment shown in FIGS. 2–4 comprises a battery 17 for the current supply to the heating members 7. This battery 17 may suitably be rechargeable and charged via an electric connection 18. The device may also comprise a built-in charging device which may be connected directly to the network.

Figure 5:
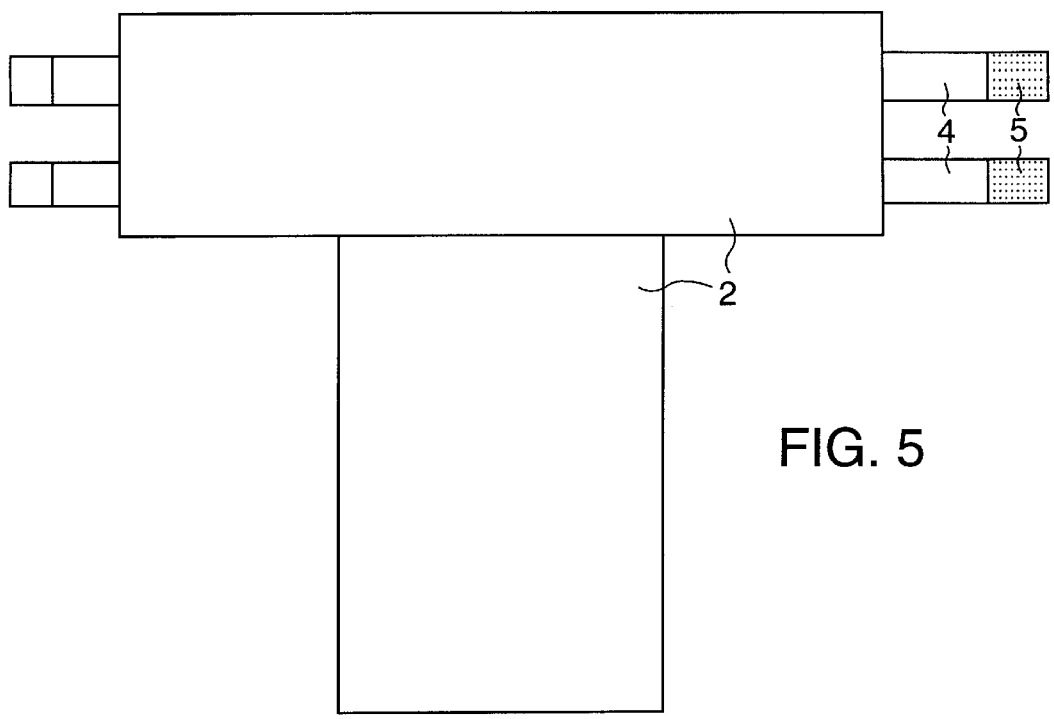
FIGS. 5–7 show different embodiments of means for holding the device according the invention against the body.
Figure 6:
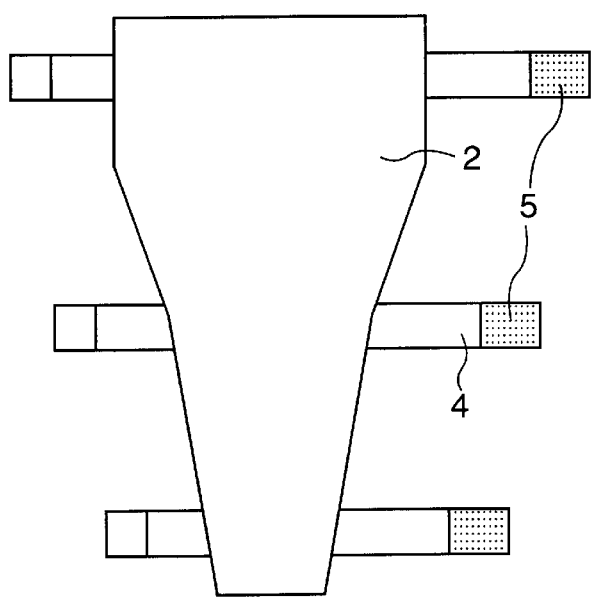
Figure 7:
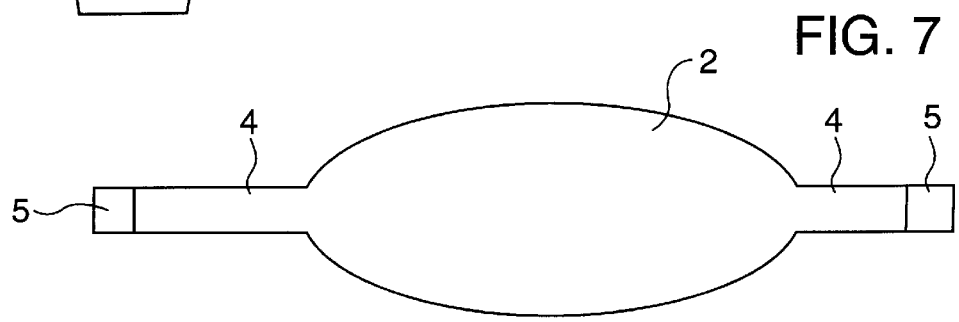

FIG. 5 shows another embodiment of the holding means 2, which is shaped for being attached around the back portion of a patient. FIG. 6 shows a further embodiment of the holding means 2, which is shaped for being attached around a leg of a patient. FIG. 7 shows a further embodiment of the holding means 2, which is particularly shaped for being attached around the lower part of the back portion, i.e. the small of the back of a patient. The holding means 2 shown in FIGS. 5–7 may be provided with one or more of the types of heating elements shown in FIGS. 1–4.

The device according to the invention is not restricted to the embodiments shown herein but may be varied and modified within the scope of the following claims. It shall also be noted that the device according to the invention is not only suitable for the heat treatment of human beings but also of animals, for example horses. It shall also be noted that one or more heating elements 1 may provide an integrated, solid part of the holding means 2, i.e. being built into the holding means.

The device according to the invention may also be used for cooling of the actual body part, for example after a hit against the body part or another kind of injury. In this case the whole device is placed in a cooling space, such as a refrigerator or the like, the liquid enclosed in the cells being chilled. Thanks to the heat storage ability of the liquid, a good refrigerating capacity may be maintained during a long period of time.

What is claimed is:

1. A device for heat treatment of a body part comprising:
   at least one heating element having a plurality of separate heating cells flexibly interconnected to each other by a broad, flexible, supporting sheet having a flat surface on which said heating cells are fixedly attached in side-by-side planar relation with an interspace located between adjacent ones of said heating cells, each said heating cell including a fluid-sealed flexible wall defining a sealed inner space;
   a heat storage means including a fluid sealed within each said sealed inner space for acting as a heat reservoir from which heat can be drawn by said body part;

a heating member including an electrical heating coil embedded within each said heat storage means for heating said heat storage means; and holding means for flexibly sandwiching said plurality of separate heating cells between said sheet and a surface of said body part such that said at least one heating element bends and substantially conforms to the shape of the surface of said body part.

2. A device according to claim 1, wherein said fluid comprises one or more of the following liquids: water, a mixture comprising glycerol, a mixture comprising oil or any oil-like substance, and a salt solution.

3. A device according to claim 1, wherein said holding means comprises an extensible, flexible material having a broad surface on which said supporting sheet is superimposed and releasibly attached by a releasable attachment member comprising hook-and-loop fasteners sandwiched between said supporting sheet and said broad surface of said holding means.

4. A device for heat treatment of a body part comprising:

a plurality of heating elements, each having a plurality of separate heating cells flexibly interconnected to each other, each said heating cell including a flexible wall defining a sealed inner space;

a heat storage means sealed within each said sealed inner space for acting as a heat reservoir from which heat can be drawn by said body part;

a heating member embedded within each said heat storage means for heating said heat storage means; and holding means for flexibly holding said heating elements against said body part, and wherein said holding means comprises an extensible, flexible material, and said plurality of heating elements mount at spaced locations on said holding means.

5. A device for heat treatment of a body part comprising:

at least three separate fluid-sealed heating cells, each said heating cell including a flexible, fluid-impermeable outer wall forming a fluid-sealed inner space;

a heat storage means, including a fluid sealed within each said fluid-sealed inner space, for acting as a heat reservoir from which heat can be drawn by said body part;

a plurality of heating members for heating said heat storage means, each said heating member including an electrical heating coil located within said fluid of a different one of said fluid-sealed inner spaces;

a flat flexible supporting sheet having a broad, planar surface to which said heating cells are fixedly attached in a two-dimensional planar array, said heating cells positioned in side-by-side relation with interspaces located between adjacent ones of said heating cells; and holding means for flexibly pressing said planar array of said heating cells against a surface of said body part such that said planar array bends and conforms to the shape of said body part.

6. A device according to claim 5, wherein said holding means comprises an extensible, flexible material having a broad flat surface on which said supporting sheet is superimposed and is releasibly attached thereto by a releasable attachment member that comprises hook-and-loop fasteners sandwiched between said supporting sheet and said broad surface of said holding means.

7. A device for heat treatment of a body part comprising:

at least four separate fluid-sealed heating cells, each said heating cell including a flexible, fluid-impermeable outer wall forming a fluid-sealed inner space;

a heat storage means, including a fluid sealed within each said fluid-sealed inner space, for acting as a heat reservoir from which heat can be drawn by said body part;

a plurality of heating members for heating said heat storage means, each said heating member including an electrical heating coil located within said fluid of a different one of said fluid-sealed inner spaces;

a flat flexible supporting sheet having a broad, planar surface to which said heating cells are fixedly attached in a two-dimensional rectangular array having at least two rows with at least two heating cells located in each row, and wherein said heating cells are positioned in side-by-side relation with interspaces located between adjacent ones of said heating cells; and holding means for flexibly pressing said array of said heating cells against a surface of said body part such that said array bends and conforms to the shape of said body part.

8. A device for heat treatment of a body part comprising:

a plurality of heating elements and at least eight fluid-sealed heating cells, wherein each said heating element includes a flat, flexible, supporting sheet with an extended planar surface on which at least four of said fluid-sealed heating cells are fixedly attached in a rectangular array having at least two rows with at least two heating cells located in each row, and wherein each said fluid-sealed heating cell includes a flexible, fluid-impermeable outer wall forming a fluid-sealed inner space;

a separate heat storage means including a fluid sealed within each said fluid-sealed inner space for acting as a heat reservoir from which heat can be drawn by said body part;

a plurality of heating members each including an electrical heating coil located within a different one of each said inner space for heating said fluid sealed therein; and holding means, having a broad flexible surface on which said heating elements are attached at spaced locations thereon, for flexibly sandwiching and pressing said heating elements between said broad surface and spaced locations of said body part such that said heating elements each bend and conform to the shapes of said spaced locations on said body part.

9. A device according to claim 8, wherein said holding means comprises an extensible, flexible material having a broad surface on which each of said heating elements is superimposed and is releasibly attached thereto by a releasable attachment member comprising hook-and-loop fasteners sandwiched between said supporting sheet and said broad surface of said holding means.

* * * * *

UNITED STATES PATENT AND TRADEMARK OFFICE
CERTIFICATE OF CORRECTION

PATENT NO. : 6,235,049 B1
DATED : May 22, 2001
INVENTOR(S) : Farzam Nazerian

It is certified that error appears in the above-identified patent and that said Letters Patent is hereby corrected as shown below:

The title, should be as follows:
A DEVICE HAVING MULTIPLE HEATING CELLS FOR HEAT TREATMENT OF A BODY PART --.

Signed and Sealed this

Twenty-seventh Day of November, 2001

Attest:

*Attesting Officer*

NICHOLAS P. GODICI
*Acting Director of the United States Patent and Trademark Office*